(12) United States Patent
Hua et al.

(10) Patent No.: US 7,205,335 B2
(45) Date of Patent: Apr. 17, 2007

(54) PREPARATION OF CIS-FUSED 3,3A,8,12B-TETRAHYDRO-2H-DIBENZO [3,4:6,7]CYCLOHEPTA[1,2-B]FURAN DERIVATIVES

(76) Inventors: Mao Hua, c/o K.U. Leuven Research & Development, Groot Begijnhof, Benedenstraat 59, Leuven (BE) B-3000; Tomasz Kozlecki, c/o K.U. Leuven Research & Development, Groot Begijnhof, Benedenstraat 59, Leuven (BE) B-3000; Frans Josef Cornelius Compernolle, c/o K.U. Leuven Research & Development, Groot Begijnhof, Benedenstraat 59, Leuven (BE) B-3000; Georges Joseph Cornelius Hoornaert, c/o K.U. Leuven Research & Development, Groot Begijnhof, Benedenstraat 59, Leuven (BE) B-3000

( * ) Notice: Subject to any disclaimer, the term of this patent is extended or adjusted under 35 U.S.C. 154(b) by 0 days.

(21) Appl. No.: 10/496,277

(22) PCT Filed: Dec. 2, 2002

(86) PCT No.: PCT/EP02/13561

§ 371 (c)(1),
(2), (4) Date: May 21, 2004

(87) PCT Pub. No.: WO03/048147

PCT Pub. Date: Jun. 12, 2003

(65) Prior Publication Data

US 2005/0033067 A1     Feb. 10, 2005

(30) Foreign Application Priority Data

Dec. 7, 2001  (EP) ................... 01204962

(51) Int. Cl.
*A61K 31/343* (2006.01)
*C07D 307/93* (2006.01)

(52) U.S. Cl. ...................... 514/468; 549/457

(58) Field of Classification Search ................ 549/457; 514/468

See application file for complete search history.

(56) References Cited

FOREIGN PATENT DOCUMENTS

WO    WO 97/38991 A1   10/1997
WO    WO 99/19317 A1    4/1999

OTHER PUBLICATIONS

Monkovic, I., et al., "Substituted Tetrahydrofurfurylamines as Potential Antidepressants" Journal of Medicinal Chemistry, 1973, vol. 16, No. 4, pp. 403-407.
Compernolle, et al., Tetrahedron Letters, "Stereoselective synthesis of transfused tetrahydrofuran derivatives of 5H-dibenzo[a,d]cycloheptene", vol. 43, pp. 3011-3015, 2002, XP002237856.

*Primary Examiner*—Bernard Dentz
(74) *Attorney, Agent, or Firm*—Woodcock Washburn LLP

(57) ABSTRACT

The present invention concerns a process for preparing each of the 4 individual diastereomers of formula (I) in stereochemically pure form from a single enantiomerically pure precursor. The tetracyclic ringsystem having cis-fused five and seven membered rings is formed in a base-catalysed cyclization reaction. The invention further relates to the thus obtained cis-fused tetracyclic alcohol intermediates and methanamine end-products, and the methanamine end-products for use as a medicine, in particular as CNS active medicines

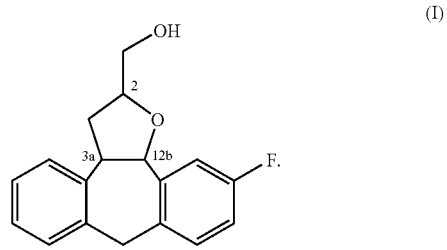

10 Claims, No Drawings

PREPARATION OF CIS-FUSED 3,3A,8,12B-TETRAHYDRO-2H-DIBENZO[3,4:6,7]CYCLOHEPTA[1,2-B]FURAN DERIVATIVES

CROSS REFERENCE TO RELATED APPLICATIONS

This application is the national stage of Application No. PCT/EP02/13561, filed Dec. 2, 2002, which application claims priority from EP 01204962.3 filed Dec. 7, 2001.

The present invention concerns processes for the preparation of each of the 4 diastereomers of cis-fused 3,3a,8,12b-tetrahydro-2H-dibenzo[3,4:6,7]cyclohepta[1,2-b]furan derivatives in stereochemically pure form from a single enantiomerically pure precursor. The tetracyclic ring system having cis-fused five and seven membered rings is formed in a base-catalysed cyclization reaction. The invention further relates to the thus obtained cis-fused tetracyclic alcohol intermediates, the methanamine end-products, the methanamine end-products for use as a medicine, in particular as CNS active medicines.

An article by Monkovic et al. (J. Med. Chem. (1973), 16(4), p. 403–407) describes the synthesis of (±)-3,3a,8,12b-tetrahydro-N-methyl-2H-dibenzo[3,4:6,7]-cyclohepta-[1,2-b]furan-2-methanamine oxalic acid. Said compound was synthesized as a potential antidepressant; however, it was found that this particular tetrahydrofurfuryl-amine derivative was inactive as an antidepressant at a dose of 300 mg/kg.

WO 97/38991, published on 23 Oct. 1997, discloses tetracyclic tetrahydrofuran derivatives of formula

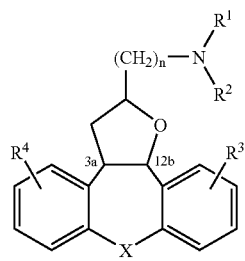

wherein the hydrogen atoms on carbon atoms 3a and 12b have the trans configuration. The 4 possible trans products are obtained from a racemic intermediate in a non-selective cyclization reaction and can be separated from one another using HPLC techniques.

WO 99/19317, published on 22 Apr. 1999, concerns halogen substituted tetracyclic tetrahydrofuran derivatives of formula

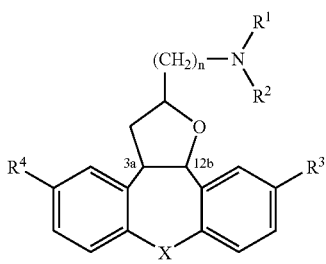

wherein the hydrogen atoms on carbon atoms 3a and 12b have the trans configuration. The 4 possible trans products are obtained from a racemic intermediate in a non-selective cyclization reaction and can be separated from one another using HPLC techniques.

As the method for preparing the trans-fused compounds proved ill-suited for upscaling, alternative routes for synthesis of these trans-fused compounds were explored, one of which opened a pathway to each of the 4 diastereomers of the previously unknown cis-fused 3,3a,8,12b-tetrahydro-2H-dibenzo[3,4:6,7]cyclohepta[1,2-b]furan derivatives.

SUMMARY OF THE INVENTION

The present invention concerns a process for preparing each of the 4 individual diastereomers of formula (I)

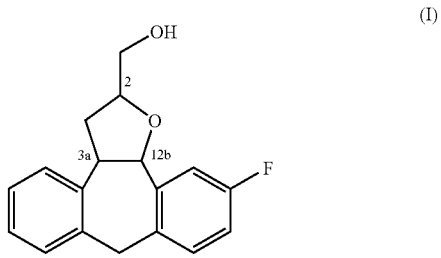

wherein the substituents on carbon atoms 3a and 12b have the cis configuration and the substituent on carbon atom 2 may have the R or the S configuration, comprising the step of cyclizing a compound of formula

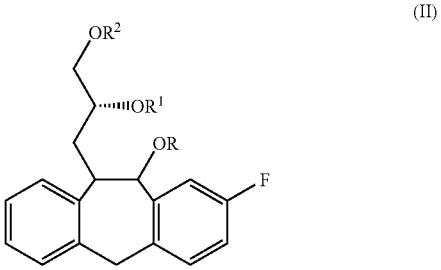

wherein R represents $C_{1-3}$alkylcarbonyl;

$R^1$ is hydrogen and $OR^2$ is a leaving group, or $OR^1$ is a leaving group and $R^2$ is hydrogen; and the substituents R and $CH_2$—$CHOR^1$—$CH_2OR^2$ have the cis configuration, in a reaction inert solvent in the presence of a base, whereby

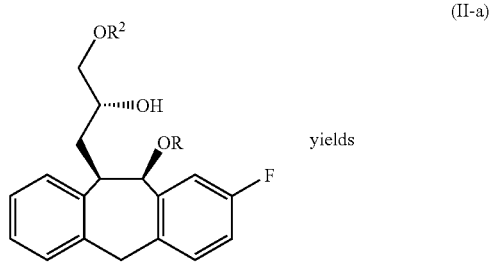

yields

-continued

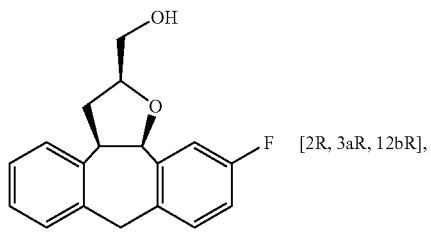
(I-a) [2R, 3aR, 12bR],

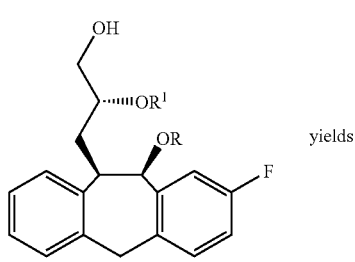
(II-b) yields

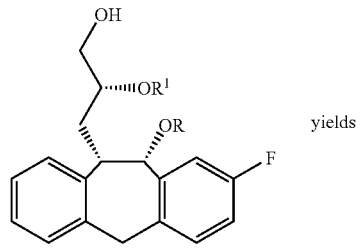
(II-d) yields

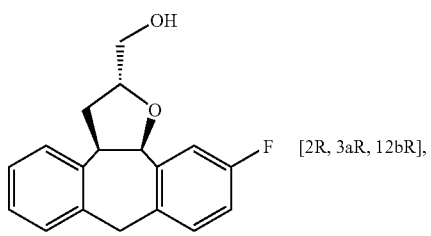
(I-b) [2R, 3aR, 12bR],

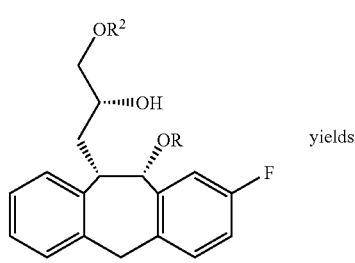
(II-c) yields

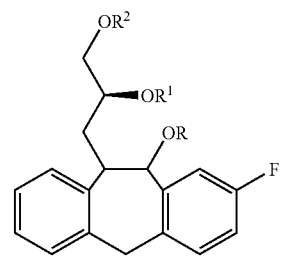
(I-d) [2R, 3aS, 12bS], or alternatively cyclizing a compound of formula

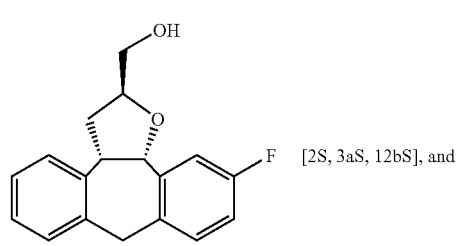
(I-c)

(ent-II)

wherein R represents $C_{1-3}$alkylcarbonyl;
$R^1$ is hydrogen and $OR^2$ is a leaving group, or
$OR^1$ is a leaving group and $R^2$ is hydrogen; and
the substituents —OR and —$CH_2$—$CHOR^1$—$CH_2OR^2$ have the cis configuration, in a reaction inert solvent in the presence of a base, whereby
(ent-II-a) yields (I-d),
(ent-II-b) yields (I-c),
(ent-II-c) yields (I-b), and
(ent-II-d) yields (I-a).

[2S, 3aS, 12bS], and

DETAILED DESCRIPTION OF THE INVENTION $C_{1-3}$alkylcarbonyl represents methylcarbonyl, ethylcarbonyl and propylcarbonyl; the term 'a leaving group' represents sulfonyloxy groups such as methanesulfonyloxy, trifluoromethanesulfonyloxy, benzenesulfonyloxy, 4-methylbenzenesulfonyloxy, 4-nitrobenzenesulfonyloxy and 4-bromobenzenesulfonyloxy. The prefix 'ent' designates the mirror image of the enantiomers of formula (II) shown hereinbefore.

Suitable solvents are, for example, alkanols, e.g. methanol or ethanol. Suitable bases are, for example, inorganic bases, e.g. potassium carbonate, particularly anhydrous potassium carbonate. The reaction can conveniently, be conducted by stirring the reagent, substrate and solvent at ambient temperature.

Under the reaction conditions, the acyl group (OR) is saponified, the hydroxyl group on the $C_3$ side chain engages in a nucleophilic substitution reaction of the vicinal carbon atom bearing the leaving group forming an intermediate epoxide, and the hydroxyl on the seven membered ring group engages in a nucleophilic substitution reaction of the nearest carbon atom of the intermediate epoxide forming a cis-fused tetrahydrofuran ring.

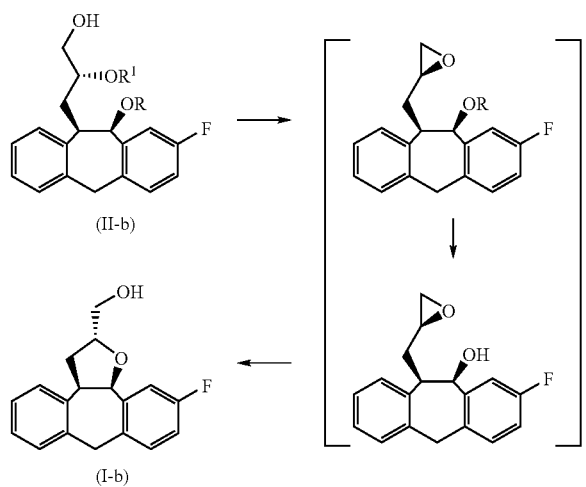

(II-b)

(I-b)

The numbering of the tetracyclic ring-system present in the compounds of formula (I), as defined by Chemical Abstracts nomenclature is shown in formula (I').

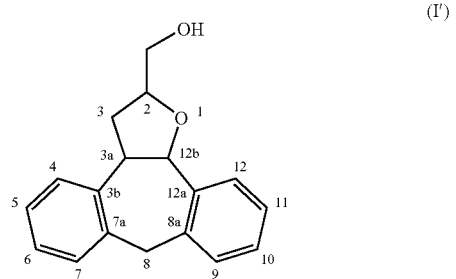

(I')

The compounds of formula (I) have at least three asymmetric centers, namely carbon atom 2, carbon atom 3a and carbon atom 12b. Carbon atoms 3a and 12b are part of an annelated ring system. In this case, where more than 2 asymmetric carbon atoms are present on a ring system, the substituent highest in priority (according to the Cahn-Ingold-Prelog sequence rules) on the reference carbon atom, which is defined as the asymmetric carbon atom having the lowest ring number, is arbitrarily always in the "α" position of the mean plane determined by the ring system. The position of the highest priority substituent on the other asymmetric carbon atoms relative to the position of the highest priority substituent on the reference atom is denominated by "α" or "β". "α" means that the highest priority substituent is on the same side of the mean plane determined by the ring system, and "β3" means that the highest priority substituent is on the other side of the mean plane determined by the ring system.

The following table summarizes the nomenclatures using absolute and relative stereodescriptors of each of the four cis-stereoisomers of the compound of formula (I).

| Absolute configuration | | | Relative configuration | | |
|---|---|---|---|---|---|
| 2 | 3a | 12b | 2 | 3a | 12b |
| R | R | R | α | α | α |
| R | S | S | α | β | β |
| S | R | R | α | β | β |
| S | S | S | α | α | α |

The tetracyclic alcohols of formula (I) can be converted further into target compounds of pharmaceutical interest by
(a) converting the primary hydroxyl group into a leaving group, and
(b) reacting the thus obtained intermediate compound of formula (IV)

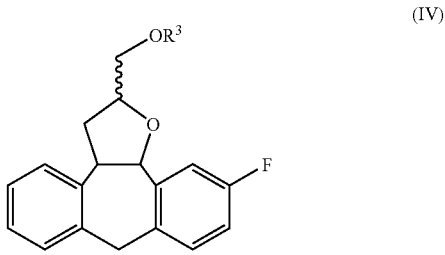

(IV)

wherein $R^3$ represents a sulfonyl group, with aqueous or gaseous methanamine in an organic solvent at an elevated temperature, thus yielding

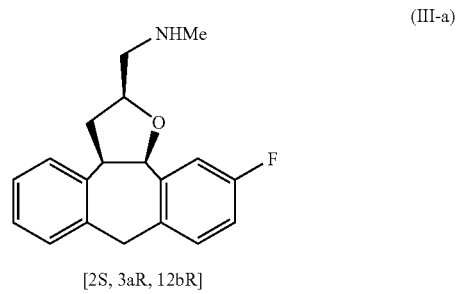

(III-a)

[2S, 3aR, 12bR]

-continued

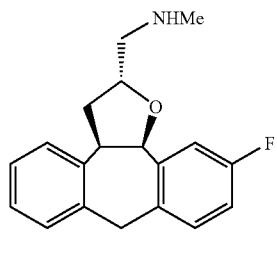

(III-b)

[2R, 3aR, 12bR]

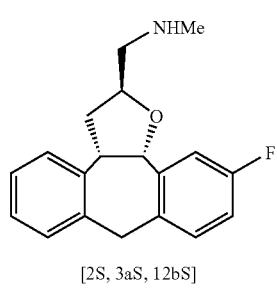

(III-c)

[2S, 3aS, 12bS]

and

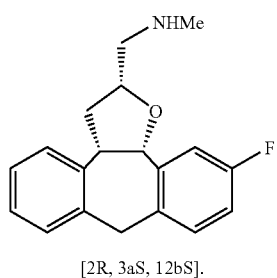

(III-d)

[2R, 3aS, 12bS].

A suitable organic solvent is for example tetrahydrofuran. The reaction is preferably conducted in a pressure vessel at a temperature in the range of 120° C. to 150° C.

Each of the intermediate compounds of formula

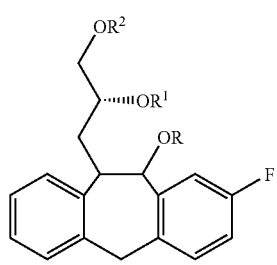

(II)

is prepared from a diol of formula

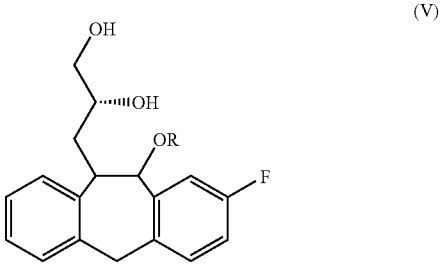

(V)

using one or more chemoselective reactions.

The intermediates of formula (II) wherein
(i) $R^1$ is hydrogen and $OR^2$ is a leaving group as defined hereinbefore, are prepared from the diol of formula (V) by chemoselective conversion of the primary hydroxyl group into a leaving group. One such method comprises stirring the diol of formula (V) in a reaction inert solvent such as a halogenated hydrocarbon, e.g. dichloromethane, in the presence of an excess of a base such as triethylamine, an equivalent of dimethylaminopyridine and half an equivalent of dibutyl(oxo)stannane, and two equivalents of tosylchloride or a similar sulfonylchloride. The reaction may also be conducted in the absence of dibutyl(oxo) stannane and dimethylaminopyridine, but then typically will yield a mixture of substrate, mono- and disubstituted product from which the desired mono-substituted compound needs to be separated.

Or, the intermediates of formula (II) wherein
(ii) $OR^1$ is a leaving group and $R^2$ is hydrogen, are prepared from the diol of formula (V) by
(1) chemoselective protection of the primary hydroxyl group with an acid labile protecting group such as a trityl group;
(2) converting the secondary hydroxyl group into a leaving group by reaction with a sulfonylchloride in a solution of dichloromethane in the presence of triethylamine and diethylaminopyridine;
(3) deprotecting the primary hydroxyl group in the thus obtained intermediate of formula (VI)

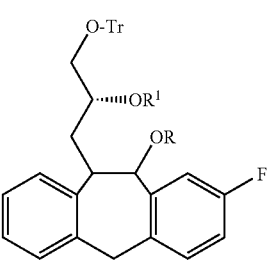

(VI)

wherein Tr represents trityl, in the presence of an acid such as an acidic ion exchange resin, e.g. Amberlyst-15, in a reaction inert solvent such as an alkanol e.g. methanol, at a temperature ranging from 40° C. to 60° C.

The overall reaction scheme for converting diol (V) into intermediate II-b thus is as follows

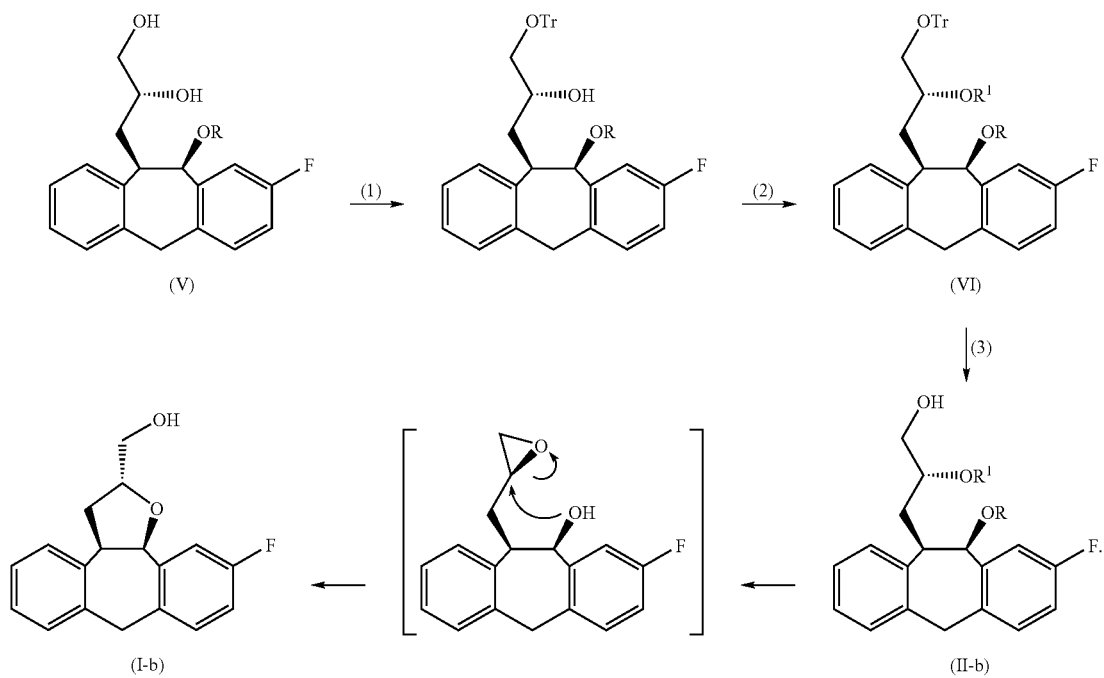

The intermediate diol of formula (V) can be prepared from a ketone of formula

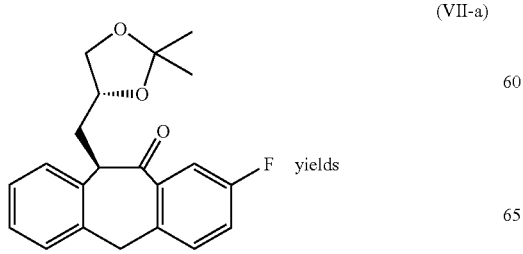

by the following series of reaction steps:
(a) reducing the ketone of formula (VII) to the cis-oriented hydroxyl group by reaction with lithium or sodium borohydride in a mixture of an organic solvent and an aqueous buffer having a pH of about 7 at a temperature below ambient temperature;
(b) acylating the hydroxyl group with an acylchloride or acyl anhydride following art-known procedures, and
(c) unmasking the diol by a deacetalisation reaction in an organic solvent in the presence of an acid, whereby

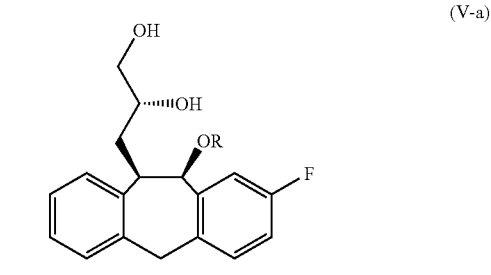

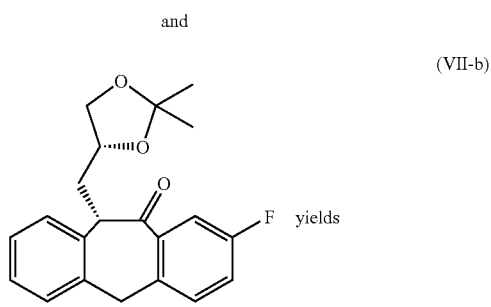

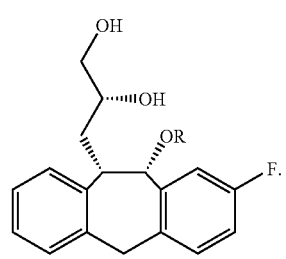

The intermediate ketones of formula (VII) are prepared from the α,β-unsaturated ketone (VIII)

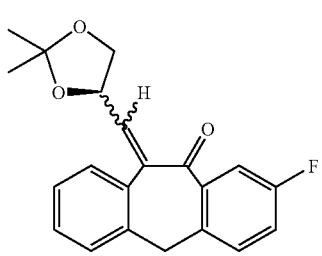

(VIII)

by either Pd/C catalyzed hydrogenation or a reduction procedure using sodiumcyanoborohydride, yielding a mixture of epimeric ketones (VII-a) and (VII-b) in a rather invariant ratio of about 3:2.

The hydrogenation reaction may conveniently be conducted in a variety of solvents such as alcohols, e.g. methanol, ethanol, isopropanol; esters, e.g. ethyl acetate; ethers, e.g. tetrahydrofuran; aromatic hydrocarbons, e.g. toluene; optionally in the presence of a tertiary amine such as triethylamine or quinine.

Reduction of (VIII) can be accomplished with sodium cyanoborohydride under slightly acidic conditions.

The epimeric ketones (VII-a) and (VII-b) can be obtained separately by chromatographic separation (diethylether/hexane 60/40). Separation can also be effected on the epimeric alcohols obtained following reduction of (VII) according to step (a).

To prepare intermediate (VIII), (4S)-2,2-dimethyl-1,3-dioxolane-4-carboxaldehyde (IX) and pro-chiral ketone (X) can be dissolved in a suitable solvent such as tetrahydrofuran and treated with a base such as tert.butyloxypotassium salt and a co-reagent such as magnesium chloride or bromide (aldol condensation).

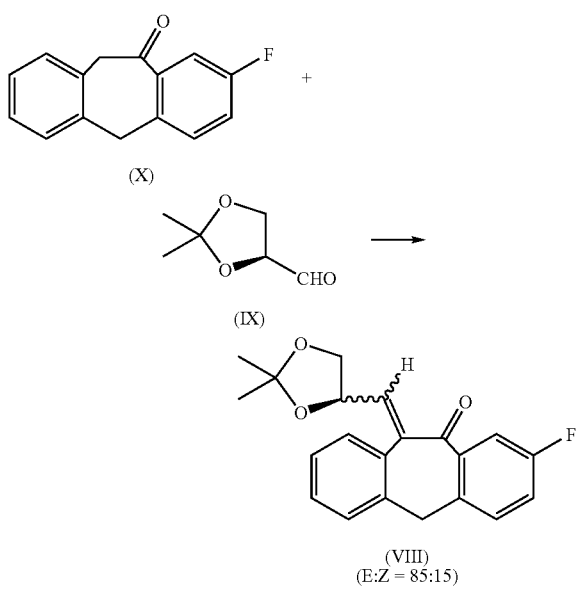

The pro-chiral ketone (X) can be prepared by adaption of an art-known sequence (Can. J. Chem., 1971, 49, 746–754) starting with a Friedel-Crafts acylation reaction using fluorobenzene and phthalic anhydride to form keto-acid (XI), followed by reductive removal of the ketone group and homologation of the carboxylic acid function.

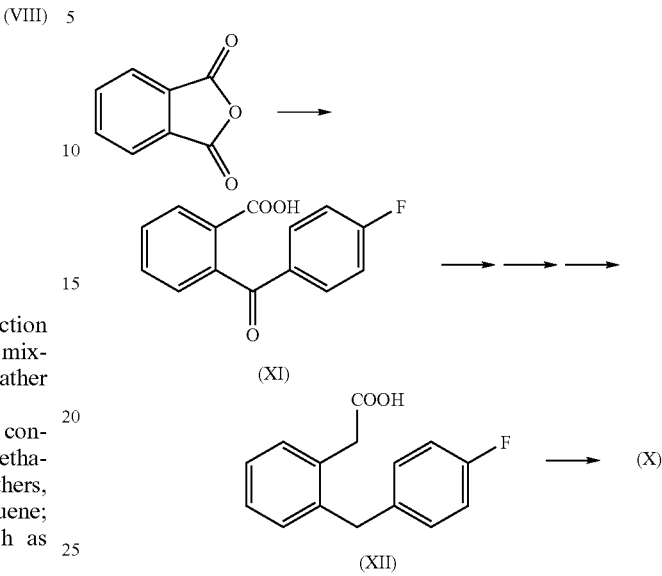

Cyclization of the homologous acid (XII) in another Friedel-Crafts acylation affords ketone (X).

The process according to the present invention provides an enantioselective approach to the target molecule (III) in enantiopure form via the enantiopure alcohols of formula (I). Both target and intermediate molecules of formulae (III) and (I) are novel.

The pharmaceutically active compounds of formula (III) may occur in their free form as a base or in a pharmaceutically acceptable salt form obtained by treatment of the free base with an appropriate non-toxic acid such as an inorganic acid, for example, hydrohalic acid, e.g. hydrochloric or hydrobromic, sulfuric, nitric, phosphoric and the like acids; or an organic acid, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The term addition salt as used hereinabove also comprises the solvates which the compounds of formula (I) as well as the salts thereof, are able to form. Such solvates are for example hydrates, alcoholates and the like.

The term 'enantiopure form' designates compounds and intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%.

The compounds of the present invention show affinity for 5-HT receptors, particularly for 5-$HT_{2A}$, 5-$HT_{2C}$ and 5-$HT_7$ receptors (nomenclature as described by D. Hoyer in "Serotonin (5-HT) in neurologic and psychiatric disorders" edited by M. D. Ferrari and published in 1994 by the Boerhaave Commission of the University of Leiden). The serotonin antagonistic properties of the present compounds may be demonstrated by their inhibitory effect in the "5-hydroxytryptophan Test on Rats" which is described in Drug Dev. Res., 13, 237–244 (1988). Furthermore, the compounds of the present invention show interesting affinity for $H_1$-receptors ($pIC_{50}$: 7.15–7.89), D2 and/or D3 receptors, and surprisingly for norepinephrine reuptake transporters ($pIC_{50}$: 6.03–7.34).

In view of these pharmacological and physicochemical properties, the compounds of formula (III are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children, aggression, memory disorders and attitude disorders in older people, addiction, obesity, bulimia and similar disorders. In particular, the present compounds may be used as anxiolytics, antipsychotics, antidepressants, anti-migraine agents and as agents having the potential to overrule the addictive properties of drugs of abuse.

The compounds of formula (III) may also be used as therapeutic agents in the treatment of motoric disorders. It may be advantageous to use the present compounds in combination with classical therapeutic agents for such disorders.

The compounds of formula (III) may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the compounds of formula (III), it follows that the present invention also provides a method of treating warm-blooded animals suffering from such diseases, said method comprising the systemic administration of a therapeutic amount of a compound of formula (III) effective in treating the above described disorders, in particular, in treating anxiety, psychosis, schizophrenia, depression, migraine, sleep disorders and addictive properties of drugs of abuse.

The present invention thus also relates to compounds of formula (III) as defined hereinabove for use as a medicine, in particular, the compounds of formula (III) may be used for the manufacture of a medicament for treating anxiety, psychosis, schizophrenia, depression, migraine, sleep disorders and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (III) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (III) due to their increased water solubility over the corresponding base or acid form, are more suitable in the preparation of aqueous compositions.

In order to enhance the solubility and/or the stability of the compounds of formula (III) in pharmaceutical compositions, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin. Also co-solvents such as alcohols may improve the solubility and/or the stability of the compounds of formula (III) in pharmaceutical compositions.

Other convenient ways to enhance the solubility of the compounds of the present invention in pharmaceutical compositions are described in WO 97/44014.

More in particular, the present compounds may be formulated in a pharmaceutical composition comprising a therapeutically effective amount of particles consisting of a solid dispersion comprising a compound of formula (III), and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions.

Such dispersions are not chemically and physically uniform throughout or comprise more than one phase.

The water-soluble polymer in the particles is a polymer that has an apparent viscosity of 1 to 100 mPa.s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Experimental Part

Hereinafter, "DMF" is defined as N,N-dimethylformamide, "THF" is defined as tetrahydrofuran, "DIPE" is defined as diisopropyl ether, "$HCl_{cp}$" is defined as chemically pure hydrochloric acid (34.5% w/w).

A. Preparation of the Intermediate Compounds

EXAMPLE A1a

Intermediate 1: 2-(4-fluorobenzoyl)benzoic acid —CAS RN [7649–29–5]

(i) A solution of p-fluorobenzenemagnesium bromide (1.2M solution in THF, 1 eq.) was added to a 0.4M solution of phthalic anhydride in THF, so that the temperature remained under 30° C. After 1 h, half of the solvent was distilled off and the reaction mixture was stirred overnight at room temperature. The obtained precipitate was filtered off and taken up in water (0.3 L/mol). Toluene (1 L/mol) and $HCl_{cp}$ were added so that the temperature remained under 35° C. After stirring 1 h, the organic layer was evaporated (50° C., vac.) and the obtained solid was dried at 50° C. under vacuum.

Physical yield: 74% Purity: 93% (LC abs %)⇒ Active yield: 69% of intermediate 1

(ii) Alternatively, a Friedel-Crafts reaction can be performed:

Phthalic anhydride, fluorobenzene (1.2 eq.) and $CH_2Cl_2$ (0.5 L/mol) were mixed at room temperature. $AlCl_3$ (0.8 eq.) was added over 60 min. (at 1 mol scale). After 5 h at room temperature, the mixture was heated up to reflux during 18 h, then cooled down to room temperature and poured very slowly in ice/water and stirred during 1 h. The organic layer was separated and the water layer was extracted with $CH_2Cl_2$ (0.25 L/mol)

The combined organic layers were washed with water (0.3 L/mol), then extracted with 320 ml water (0.7 L/mol)/NaOH 50% (0.07 L/mol). The water layer was separated and washed with 60 ml $CH_2Cl_2$ (0.15 L/mol) Norit-A-Supra (active charcoal) (10 g/mol) was added and the mixture was stirred and filtered.

Water (0.7 L/mol)/$HCl_{cp}$ (2.5 eq.) solution was added dropwise, the mixture was stirred during 30 min., the precipitate filtered off, washed with water (2×0.2 L/mol) and dried.

Yield: 92% of intermediate 1.

EXAMPLE A1b

Intermediate 2: 2-[(4-fluorophenyl)methyl]benzoic acid— CAS RN [346474]

Intermediate 1 was dissolved in isopropanol (2 L/mot) and Pd/C (10% dry) was added. The reaction mixture was heated up to 45° C. and hydrogenated overnight at atmospheric pressure. After cooling the flask to room temperature, the catalyst was filtered off over diatomaceous earth and rinsed with 30 ml isopropanol. The filtrate was evaporated at 45° C. under vacuum.

Physical yield: 98% Purity: 96.4% (LC abs %)⇒ Active yield: 94% of intermediate 2

EXAMPLE A1c

Preparation of Intermediate 3

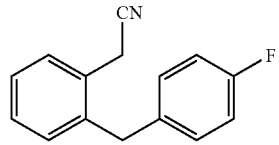

Intermediate 2 was dissolved in toluene (1.5 L/mol) and DMF (1 ml/mol) was added. The reaction mixture was heated up to 40° C. and thionyl chloride (1.1 eq.) was added. During the addition the reaction mixture was further heated up to 50° C. The reaction mixture was stirred at 50° C. during 2 h 30, then evaporated at 50° C. under vacuum. THF (0.3 L/mol) was added and that solution was dropped into a 2M $NaBH_4$ solution in THF (1.5 eq.). The temperature rose to reflux (67° C.) and the reaction mixture was stirred at reflux during 2 h. The reaction mixture was cooled down to room temperature. Aceton (350 ml/mol) was added (temperature rose to 40° C.), the reaction mixture was stirred during 30 minutes, followed by toluene (1 L/mol) and water (1.5 L/mol). The reaction mixture was heated up to 50° C. and the organic layer evaporated at 50° C. under vacuum. $CH_2Cl_2$ (3 L/mol) was added, followed by triethylamine (1.1 eq.). $SOCl_2$ (1.1 eq.) was added dropwise, the temperature rose to reflux. The reaction mixture was stirred during 45 min to room temperature. Water (1 L/mol) was added and the reaction mixture was stirred vigorously during 15 min. The organic layer was washed a second time with water (1 L/mol) and evaporated (40° C., vac.). The product was dissolved in toluene (2.5 L/mol), tetrabutylammonium hydrogenosulfate (phase-transfer reagent) (0.1 eq.) was added at 70° C. NaCN 6M (1.6 eq.) was added at 70° C. under vigorous stirring. The reaction mixture was then heated up to reflux and stirred 3 h. After cooling down to room temperature, water (0.5 L/mol) was added, the reaction mixture was stirred during 30 minutes. After washing a second time with water (0.5 L/mol), drying on $MgSO_4$ and evaporating the solvent, intermediate 3 was obtained.

Physical yield: 98% Purity: 96.4% (LC abs %)⇒ Active yield: 94% of intermediate 3

EXAMPLE A1d

Preparation of Intermediate 4

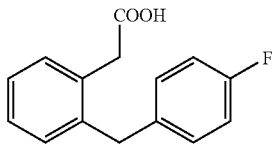

Intermediate 3 was suspended in acetic acid (0.5 L/mol), water (0.3 L/mol) and sulfuric acid (0.35 L/mol). After 5 h at reflux, the mixture was cooled down, water (1.2 L/mol) and dichloromethane (0.3 L/mol) were added. The organic extract was washed with water (1.3 L/mol) and NaOH 50% (0.15 L/mol). After stirring 20 min., the aqueous layer was separated and washed with $CH_2Cl_2$ (0.1 L/mol), which was discarded. The aqueous layer was acidified with $HCl_{cp}$ (2 eq.). The mixture was stirred during 3 h, the precipitate was then filtered off and washed with water (0.1 L/mol).

Yield: 74% of intermediate 4

EXAMPLE A1e

Preparation of Intermediate 5

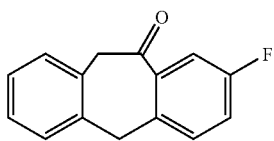

Intermediate 4 was dissolved in dichloromethane (0.6 L/mol) and N,N-dimethyl acetamide, 15 ml/mol). Thionyl chloride (1 eq.) was added dropwise and the reaction mixture was refluxed during 1 h30. After cooling down to 0° C., $AlCl_3$ (1 eq.) was added and the mixture was stirred during 2 h. HCl, (2 eq.) and water (0.3 L/mol) were added. The layers were separated, the organic layer was washed with 5% $NaHCO_3$ solution (0.6 L/mol), then with water. The organic layer was evaporated, isopropanol (0.25 L/mol) was added. The mixture was heated up to reflux (30 min.) and cooled down. Seeding occured at 65° C. After cooling down further and stirring 2 h at rt, the precipitate was filtered off, washed with isopropanol (0.05 L/mol) and dried at 50° C. under vacuum.

Yield: 40–80% of intermediate 5. Typical purity between 77% and 93%

EXAMPLE A1f

Preparation of Intermediate 6

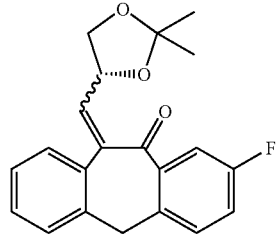

Intermediate 5 was dissolved in toluene (2 L/mol). $MgCl_2$ anhydrous (1.2 eq.) was added and the reaction mixture was stirred at room temperature during 30 min. (S)-solketal aldehyde (from DSM, 1.7 eq., 20% solution in THF) was added and in one time 0.2 eq. potassium tert-butoxide. Slight exothermicity was observed. The reaction mixture was stirred during 68 h at room temperature. Water (0.5 L/mol) was added, followed by 0.2 eq. $HCl_{cp}$. The reaction mixture was stirred vigorously during 5 min. The organic layer was washed again with 0.5 L/mol water, then again with 1 L/mol water. After adding $Na_2SO_4$ (125 g/mol), active carbon (40 g/mol), the mixture was filtered, the remaining solid was rinsed with toluene (0.2 L/mol) and the filtrate was evaporated. Isopropanol (1.5 L/mol) was added, the reaction mixture was stirred at least 8 h at 20–25° C., then cooled down to 0–5° C. and stirred at that temperature for at least 2 h. The precipitate was filtered off, washed with cold isopropanol (0.07 L/mol) and air-dried at 40° C.

Physical yield: 58% Purity: 93.1% (LC abs %)⇒ Active yield: 54% of intermediate 6.

The product could be recrystallized from iPrOH.

EXAMPLE A1g

Preparation of Intermediate 7

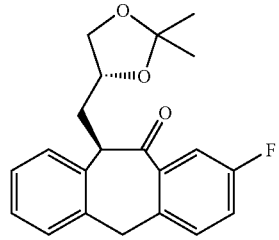

Intermediate 6 was dissolved in acetone (2 L/mol), triethylamine (1 eq.) and thiophene (4% solution in EtOH, 0.007 L/mol.) were added. After suspending Pd/C (60 g/mol, 10% wet), the hydrogenation was performed. In case the conversion was low, another 60 g/mol Pd/C was added and the hydrogenation was continued till complete conversion. Some exothermicity was observed (temperature rises to 35° C.). When the reaction was completed, the catalyst was filtered off over diatomaceous earth and the solid was rinsed with acetone (0.07 L/mol). The filtrate was evaporated (atm.) at 75–80° C. The residue was cooled down to 70–75° C. Isopropanol was added (0.84 L/mol), then evaporated again. The reaction mixture was cooled down. At 45–50° C., triethylamine (1 eq.) was added to the heterogeneous mixture. After stirring at least 8 h at 45–50° C., the mixture was cooled down to 20–25° C., stirred 2–16 h at 20–25° C., cooled down to 0–5° C. and stirred at that temperature during 2–16 h. The precipitate was filtered off, washed with cold isopropanol (0.07 L/mol) and dried during 16 h at 50° C. under vacuum. A light rose solid was obtained.

Physical yield: 83% of intermediate 7.

EXAMPLE A2a

Preparation of Intermediate 8

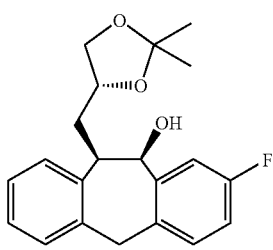

In THF (1.4 L/mol), a buffer solution of pH 7 containing potassium dihydrogenphosphate and disodium hydrogenphosphate, 0.3 L/mol was added. The mixture was cooled down to 0–5° C. and intermediate 7 was added. Lithium borohydride 2N in THF (0.48 eq.) was added and the temperature was maintained under 10° C. After the addition, the reaction mixture was stirred during 2 h at 0–5° C. Acetone (1.7 eq.) was is cautiously added and the reaction mixture was stirred to room temperature. Water (0.7 L/mol) was added at 10–25° C. and the reaction mixture was stirred 30 min. at room temperature. Acetic acid (2.2 eq.) and 200 ml toluene were added. After stirring during 10 min., the organic layer was washed with water (0.36 L/mol) and NaOH 50% (2.2 eq.), then washed again twice with water (0.45 L/mol). The solution was evaporated (a viscous oil was obtained) and dichloromethane (1 L/mol) was added. The solution was used further in the next step, assuming that 100% intermediate 8 had been obtained.

EXAMPLE A2b

Preparation of Intermediate 9

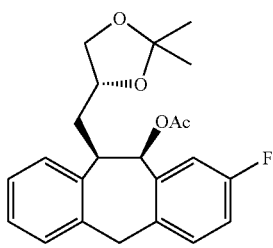

Dimethylaminopyridine (0.05 eq.) and triethylamine (1.1 eq.) were added to intermediate 8 (solution in CH$_2$Cl$_2$). Acetic anhydride (1.1 eq.) was added dropwise. The temperature was allowed to rise to 40° C. The reaction mixture was stirred during 2 h and NH$_4$Cl 1N (0.5 eq.). About 90% of the solvent was distilled off (atmospheric pressure) and isopropanol (1 L/mol) was added. About one fifth of the solvent was evaporated (atmospheric pressure) and the reaction mixture was slowly cooled down to room temperature and stirred overnight. After cooling down further to 0–5° C. and stirring at that temperature during 8–16 h, the precipitate was filtered off and washed with isopropanol (0.2 L/mol). The product was dried for 16 h at 50° C. under vacuum.

Active yield: 80% of intermediate 9.

EXAMPLE A2c

Preparation of Intermediate 10

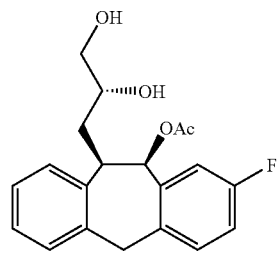

Intermediate 9 was suspended in water (0.3 L/mol) and glacial acetic acid (0.45 L/mol) was added. This mixture was stirred at 55° C. for 8 hours. The reaction proceeded to 93% conversion. The reaction mixture was cooled to ambient temperature. Water (1.5 L/mol) and methylene chloride (0.8 L/mol) were charged and the mixture was stirred for 15 minutes. The water phase was separated and extracted three times with methylene chloride (each time with 0.6 L/mol). The combined organic phases were washed with water (1 L/mol) and dried over sodium sulfate. The solvent was evaporated, yielding a fluffy white solid.

Active yield: 94% of intermediate 10.

EXAMPLE A2d

Preparation of intermediate 11

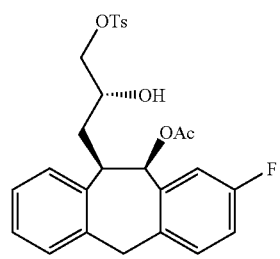

Intermediate 10 was dissolved in toluene (3.5 L/mol) and p-toluenesulfonyl chloride (1.5 eq.) was added in one portion. To this mixture, pyridine (10 eq.) was added dropwise. The reaction mixture was stirred 4 h at 40° C. Water (1.5 L/mol) was added, followed by 1 M ammonium chloride (1.3 eq.). After drying the organic phase over sodium sulfate, the organic solvent was evaporated yielding crude product, which was a mixture of starting material (8%), monotosylate (76%) and di-tosylate (16%) (LC area %).

Yield: 61% of intermediate 11.

EXAMPLE A2e

Preparation of intermediate 12

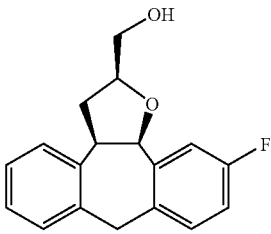

To a solution of intermediate 11 (0.62 g, 1.23 mmol) in MeOH (30 mL) was added K₂CO₃ (0.34 g, 2.46 mmol) and the mixture was stirred at room temperature for 1 day. 25 mL NH₄Cl (sat. aq. solution) was added, extracted 3 times with CH₂Cl₂ (3×20 mL) and then dried on MgSO₄. Column purification on silica gel using ether/hexane (70:30) gave intermediate 12 as a white crystalline product (0.32 g, 90%) (mp. 157–158° C.).

EXAMPLE A2f

Preparation of intermediate 13

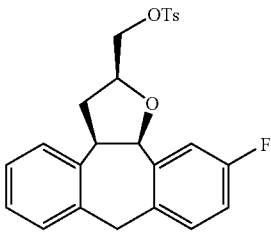

Intermediate 12 (0.31 g, 1.09 mmol) in CH₂Cl₂ was dissolved. Et₃N (0.46 ml, 3.28 mmol), DMAP (64 mg, 0.55 mmol) and TsCl (0.32 g, 1.64 mmol) were added. The solution was stirred at room temperature for 3 hr. NH₄Cl (sat. aq. sol.) was added and the aqueous layer was extracted 3 times with CH₂Cl₂ and dried with magnesium sulfate. Column purification on silica gel with Ether/Hexane (60/40) gave an yellowish oil. Yield: 0.46 g of intermediate 13 [(2S, 3aR, 12bR)-11-fluoro-3,3a,8–12b-tetrahydro-2H-dibenzo[3,4:6,7]cyclohepta[1,2-b]furan-2-yl]methyl 4-methylbenzenesulfonate (96%).

EXAMPLE A3

Preparation of Intermediate 14

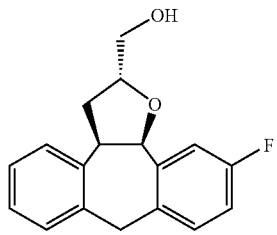

Acetate diol (intermediate 10) (826 mg, 2.39 mmol) was dissolved in CH₂Cl₂ (12 ml). Et₃N (4 ml) and Ph₃CCl (1.50 g, 5.38 mmol) were added and stirred at room temperature for 6 hr. NH₄Cl (sat. aq. sol.) was added. The mixture was extracted 3 times with CH₂Cl₂ and dried with MgSO₄. The solution was evaporated. Column purification on silica gel using ether/hexane (40/60) gave an oil (0.95 g, 68%). The above oil was dissolved in CH₂Cl₂, Et₃N (2.2 ml, 1.58 mmol), DMAP (190 mg, 1.56-mmol) and MsCl (190 μl 2.45 mmol) were added. The reaction mixture was stirred at room temperature for 2 hr. NH₄Cl (sat. aq. sol.) was added, the mixture was extracted 3 times with CH₂Cl₂ and dried with MgSO₄. Column purification on silica gel by using ether/hexane (40/60) gave an oil (900 mg, 84%). This oil (840 mg, 1.26 mmol) was dissolved in MeOH (25 ml), Amberlyst (4.5 g) was added and heated at 50° C. for 3 hr. The Amberlyst was filtered off and evaporated. The remaining oil was dissolved in MeOH (15 ml) and K₂CO₃ (1.68 g, 10.0 mmol) was added. The reaction mixture was stirred at room temperature for 18 hr. NH₄Cl was added and extracted 3 times with CH₂Cl₂ and dried with MgSO₄. Column purification on silica gel by using ether gave a white crystalline compound (Yielding: 330 mg of intermediate 14 [(2R, 3aR, 12bR)-11-fluoro-3,3a,8,12b-tetrahydro-2H-dibenzo[3,4:6,7]cyclohepta[1,2-b]furan-2-yl]methanol, 92%).

Table 1 lists the intermediates that were prepared according to one of the above Examples.

TABLE 1

| Int. No. | Ex. No. | Structure | Physical data |
|---|---|---|---|
| 1 | A2f | (structure) | 2S, 3aR, 12bR; mp.: 157–158° C. |

TABLE 1-continued

| Int. No. | Ex. No. | Structure | Physical data |
|---|---|---|---|
| 2 | A3 | 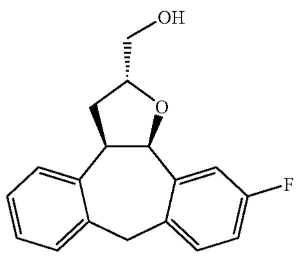 | 2R, 3aR, 12bR; mp. 99–101° C. |
| 3 | A3 | 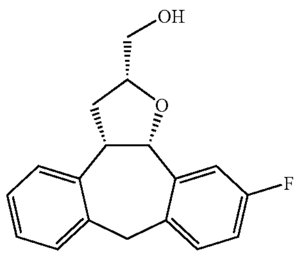 | 2R, 3aS, 12bS; $^1$H NMR: 1.90(br s, 1H, OH), 2.05 (ddd, 1H, J = 12.6, 9.6, 8.4 Hz, CH$_2$-3), 2.48(ddd, 1H, J = 12.6, 8.4, 3.6 Hz, C$\underline{H}_2$'-3), 3.70–3.80(m, 2H, CH$_2$OH), 3.81(d, 1H, J = 14.2 Hz, CH$_2$-8), 3.94(q, 1H, J ≅ 8.1 Hz, CH-3a), 4.04(d, 1H, J = 14.4 Hz, CH$_2$'-8), 4.48(m, 1H, CH-2), 5.62(d, 1H, J = 8.1 Hz, CH-12b), 6.84(dt, 1H, J = 2.6, 8.2 Hz, Ar—H-10), 6.87(dd, 1H, J = 8.1, 2.7 Hz, Ar—H-4), 7.07–7.20(m, 5H, Ar—H). |
| 4 | A2f | 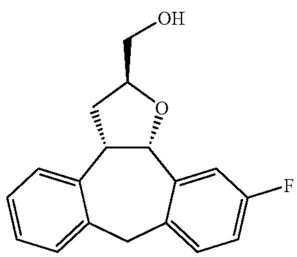 | 2S, 3aS, 12bS; $^1$H NMR: 2.02(br s, 1H, OH), 2.02–2.12(m, 1H, CH$_2$-3), 2.49(ddd, 1H, J = 12.9, 8.0, 3.9 Hz, CH$_2$'-3), 3.67–3.76(m, 1H, C$\underline{H}_2$—OH), 3.78–3.86(m, 1H, C$\underline{H}_2$'—OH), 3.83(d, 1H, J = 14.1 Hz, CH$_2$-8), 3.94(q, 1H J ≅ 8.8 Hz, CH-3a), 4.05(d, 1H, J = 14.1 Hz, CH$_2$'-8), 4.45–4.54(m, 1H, CH-2), 5.63(d, 1H, J = 7.3 Hz, CH-12b), 6.84(dt, 1H, J = 2.9, 8.4 Hz, Ar—H-10), 7.08–7.20(m, 6H, Ar—H). |

B. Preparation of the Final Compounds

EXAMPLE B1

Preparation of Compound 1

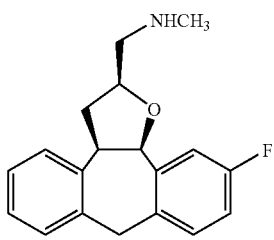

The tosylated compound (intermediate 13) (0.46 g, 1.05 mmol) was dissolved in THF (15 ml) and 40% CH$_3$NH$_2$ solution (15 ml) was added. The reaction mixture was brought into a tightly sealed steel vessel and heated at 130° C. for 12 hr. The mixture was cooled down to room temperature and NH$_4$Cl (sat. aq. sol.) was added. The solution was extracted 3 times with CH$_2$Cl$_2$ and dried with MgSO$_4$. After evaporation, the residue was purified on silica gel column with MeOH/CHCl$_3$ (15/85) to give an yellowish oil (Yield: 0.30 g, 97% of compound 1 [(2S,3aR,12bR)-11-fluoro-3,3a,8,12b-tetrahydro-2H-dibenzo[3,4:6,7]cyclohepta[1,2-b]furan-2-yl]-N-methylmethanamine).

EXAMPLE B2

Preparation of Compound 2

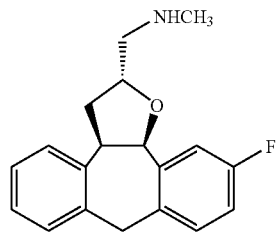

To a solution of alcohol (intermediate 14) (172 mg, 0.605 mmol) in CH$_2$Cl$_2$(15 mL) was added TsCl (0.20 g, 1.05 mmol), Et$_3$N (0.25 mL, 1.80 mmol), DMAP (37 mg, 0.303 mmol). The reaction mixture was stirred at room temperature for 2 hr. 15 mL NH$_4$Cl (sat. aq. solution) was added. The mixture was extracted 3 times with CH$_2$Cl$_2$ (3×15 mL) and dried with MgSO$_4$. Column purification on silica gel by using ether/Hexane (60:40) gave an oil (0.26 g, 95%). To this oil (0.26 g, 0.571 mmol) in THF (15 mL) was added 40% MeNH$_2$ aqueous solution (15 mL). This solution was put into a tightly sealed steel vessel and heated at 130° C. for 12 hr. After cooling down to room temperature 15 mL NH$_4$Cl (sat. aq. solution) was added. The solution was extracted 3 times with CH$_2$Cl$_2$ (3×15 mL) and dried with MgSO$_4$. Column purification on silica gel using MeOH/

CHCl₃ (15:85) yielded a yellow solid (Yielding: 0.16 g, 94% of compound 2 [(2R,3aR,12bR)-11-fluoro-3,3a,8,12b-tetrahydro-2H-dibenzo[3,4:6,7]cyclohepta[1,2-b]furan-2-yl]-N-methylmethanamine).

Table 2 lists the compounds that were prepared according to one of the above Examples.

wherein the substituents on carbon atoms 3a and 12b have the cis configuration, the substituent on carbon atom 2 may have the R or the S configuration, comprising the step of cyclizing a compound of formula (II)

TABLE 2

| Comp No. | Ex. No. | Structure | Physical data |
|---|---|---|---|
| 1 | B1 | 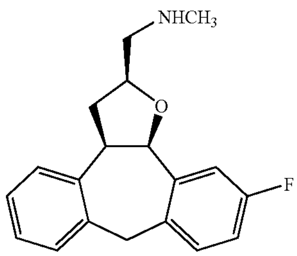 | 2S, 3aR, 12bR: Mass spectrum: CI m/z(assignment, relative intensity) 298 (MH⁺, 100%) EI: m/z(assignment, relative intensity) 297(M⁺, 12%), 209(100%) High resolution EI Calculated $C_{19}H_{20}FNO(M^+)$: 297.1529 Found: 297.1526 (56%) |
| 2 | B2 | 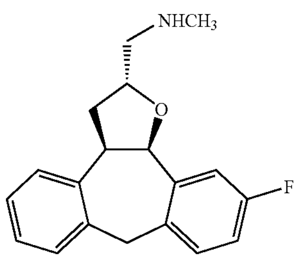 | 2R, 3aR, 12bR; mp. 214–215° C. |
| 3 | B2 | 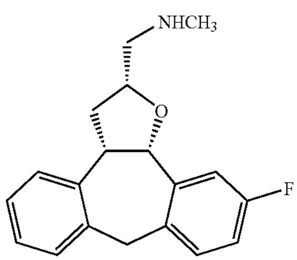 | 2R, 3aS, 12bS; ¹HNMR: 2.11(ddd, 1H, J = 12.5, 10.0, 8.7 Hz, CH₂-3), 2.41(ddd, 1H, J = 12.5, 8.7, 3.8 Hz, CH₂'-3), 2.50(br s, 1H, NH), 2.58(s, 3H, CH₃) 2.78–2.96(m, 2H, C$\underline{H}_2$NHMe), 3.79(d, 1H, J=14.6 Hz, CH₂-8), 3.90(q, 1H, J ≅ 8.6 Hz, CH-3a), 3.99(d, 1H, J=14.6 Hz, CH₂'-8), 4.41–4.51(m, 1H, CH-2), 5.57(d, 1H, J = 7.5 Hz, CH-12b), 6.80(dt, 1H, J = 2.5, 8.4 Hz, Ar—H-b), 7.06 |
| 4 | B1 | 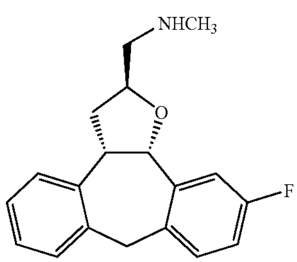 | 2S, 3aS, 12bS; ¹H NMR: 2.06–2.16(m, 1H, CH₂-3), 2.29(s, 1H, NH), 2.40(ddd, 1H, J=12.6, 7.9, 3.6 Hz, CH₂'-3), 2.54(s, 3H, CH₃), 2.72–2.90(m, 2H, C$\underline{H}_2$NHMe), 3.82(d, 1H, J = 14.3 Hz, CH₂-8), 3.91(q, 1H, J ≅ 8.3 Hz, CH-3a), 4.02(d, 1H, J=14.3 Hz, CH₂'-8), 4.48–4.58(m, 1H, CH-2), 5.57(d, 1H, J = 7.3 Hz, CH-12b), 6.82(dt, 1H, J = 2.8, 8.3 Hz, Ar—H-10), 7.06–7.20 (m, 6H, Ar—H) |

The invention claimed is:

1. A process for preparing each individual diastereoisomer of formula (I):

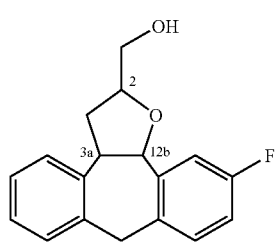

(I)

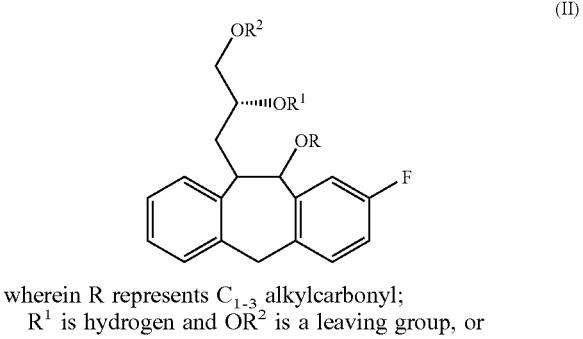

(II)

wherein R represents $C_{1-3}$ alkylcarbonyl;
R¹ is hydrogen and OR² is a leaving group, or OR¹ is a leaving group and
R² is hydrogen; and
the substituents —OR and —CH²—CHOR¹—CH₂OR²
  have the cis configuration, in a reaction inert solvent
  in the presence of a base, whereby

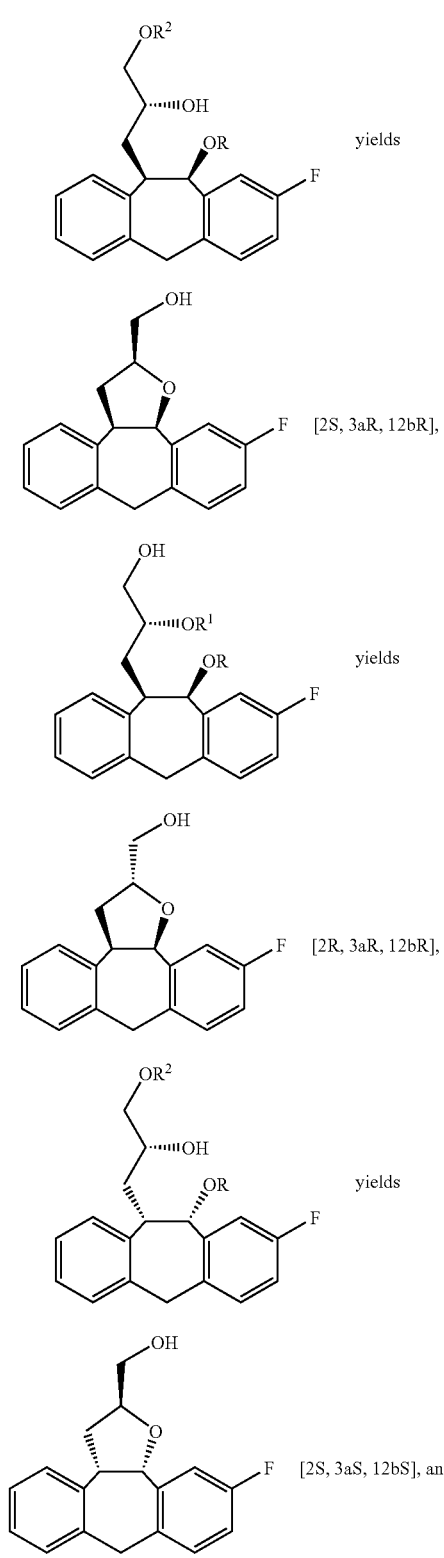

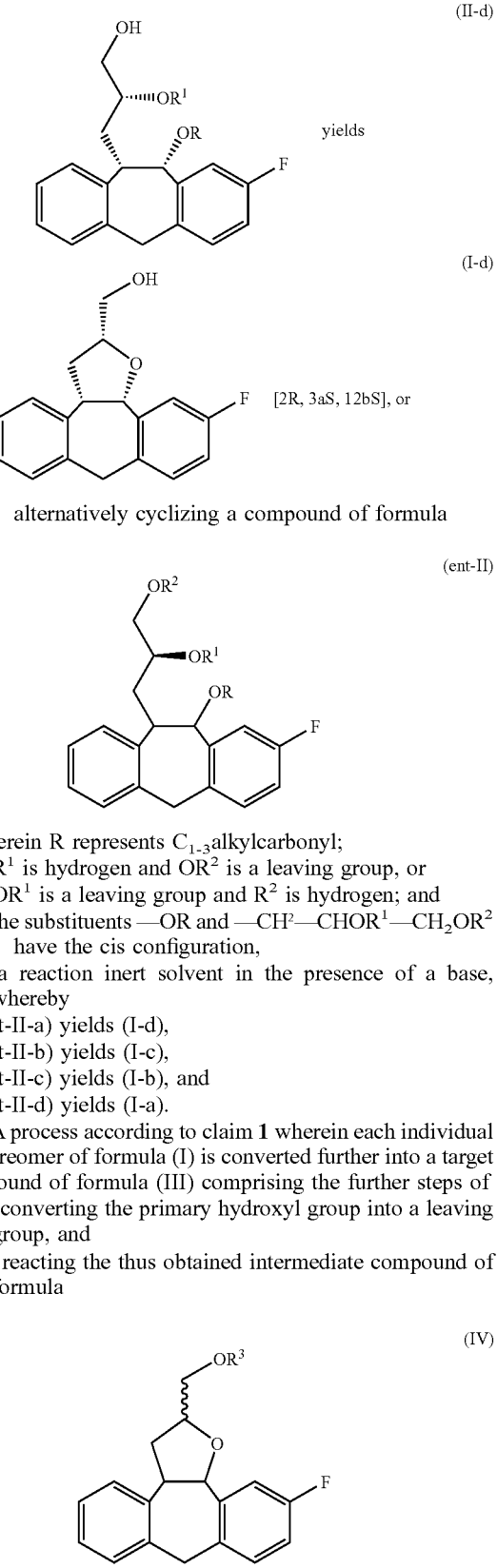

alternatively cyclizing a compound of formula wherein R represents $C_{1-3}$alkylcarbonyl;
  R¹ is hydrogen and OR² is a leaving group, or
  OR¹ is a leaving group and R² is hydrogen; and
  the substituents —OR and —CH²—CHOR¹—CH₂OR²
    have the cis configuration,
  in a reaction inert solvent in the presence of a base, whereby
  (ent-II-a) yields (I-d),
  (ent-II-b) yields (I-c),
  (ent-II-c) yields (I-b), and
  (ent-II-d) yields (I-a).

2. A process according to claim 1 wherein each individual diastereomer of formula (I) is converted further into a target compound of formula (III) comprising the further steps of
  (a) converting the primary hydroxyl group into a leaving group, and
  (b) reacting the thus obtained intermediate compound of formula wherein R³ represents a sulfonyl group with aqueous methylamine in an organic solvent at an elevated temperature, thus yielding (III-a)

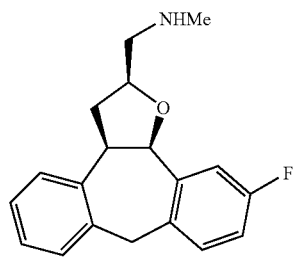

[2S, 3aR, 12bR]

(III-b)

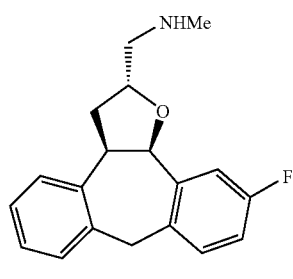

[2R, 3aR, 12bR]

(III-c)

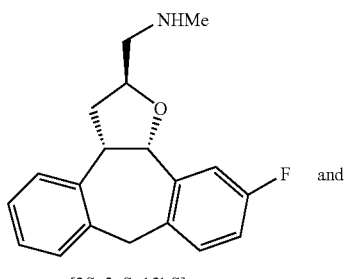

[2S, 3aS, 12bS]

and (III-d)

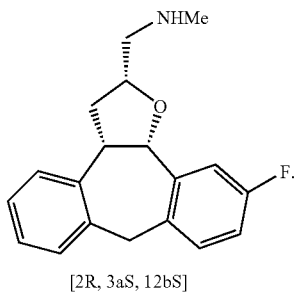

[2R, 3aS, 12bS]

3. A process according to claim 1 wherein the compound of formula (II)

(II)

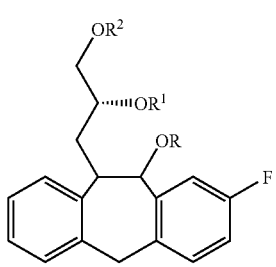

(i) wherein

R¹ is hydrogen and OR² is a leaving group
and the substituents —OR and —CH²—CHOR¹—CH₂—OR² have the cis configuration is prepared from a diol of formula (V)

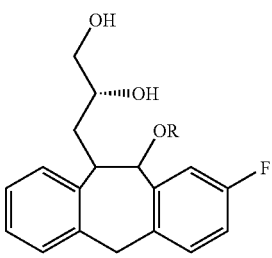

wherein the substituents —OR and —CH₂—CHOH—CH₂—OH have the cis configuration, by selective conversion of the primary hydroxyl group into a leaving group, or (ii) wherein OR¹ is a leaving group and R² is hydrogen
and the substituents —OR and —CH²—CHOR¹—CH₂—OR² have the cis configuration is prepared from a diol of formula (V)

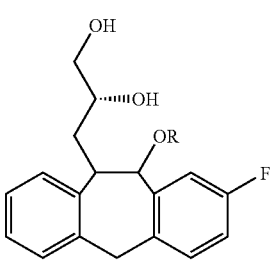

wherein the substituents —OR and —CH₂—CHOH—CH₂—OH have the cis configuration by 1) selective protection of the primary hydroxyl group with an acid labile protecting group,
2) conversion of the secondary hydroxyl group into a leaving group, and
3) deprotection of the primary hydroxyl group by treatment with an acid.

4. A process according to claim 3 wherein the intermediate diol of formula (V)

(V)

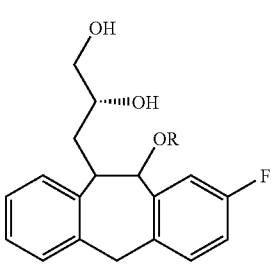

wherein the substituents have the cis configuration is prepared from a ketone of formula (VII)

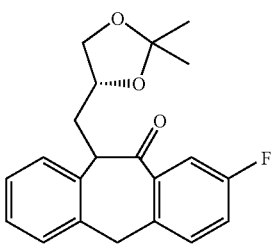

(VII)

by the following series of reaction steps
(a) reduction of the ketone to the cis-oriented hydroxyl group by reaction with lithium or sodium borohydride in a mixture of an organic solvent and an aqueous buffer having a pH of about 7 at a temperature below ambient temperature;
(b) acylation of the hydroxyl group; and
(c) deacetalisation in an organic solvent in the presence of an acid,
whereby

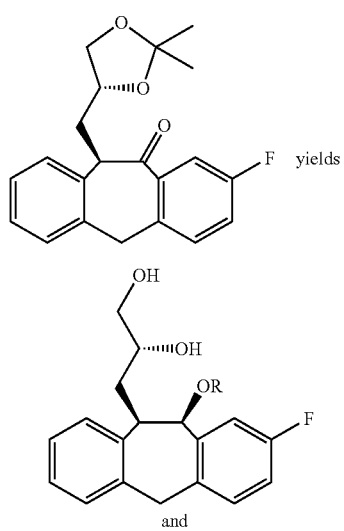

(VII-a)

yields (V-a)

and (VII-b)

yields (V-b)

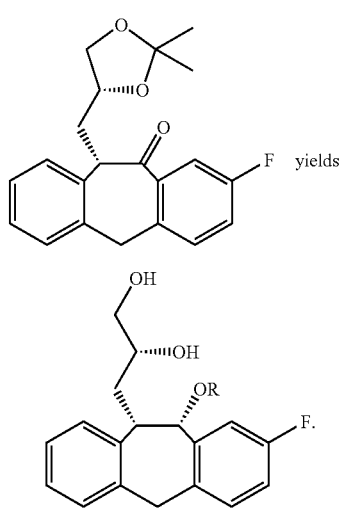

5. A process according to claim 4 wherein the ketone of formula (VII)

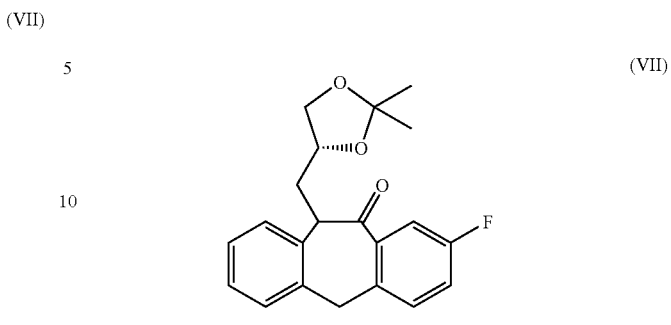

(VII)

is prepared from a pro-chiral ketone of formula (X) and (4S)-2,2-dimethyl-1,3-dioxolane-4-carboxaldehyde (IX) in an aldol reaction,

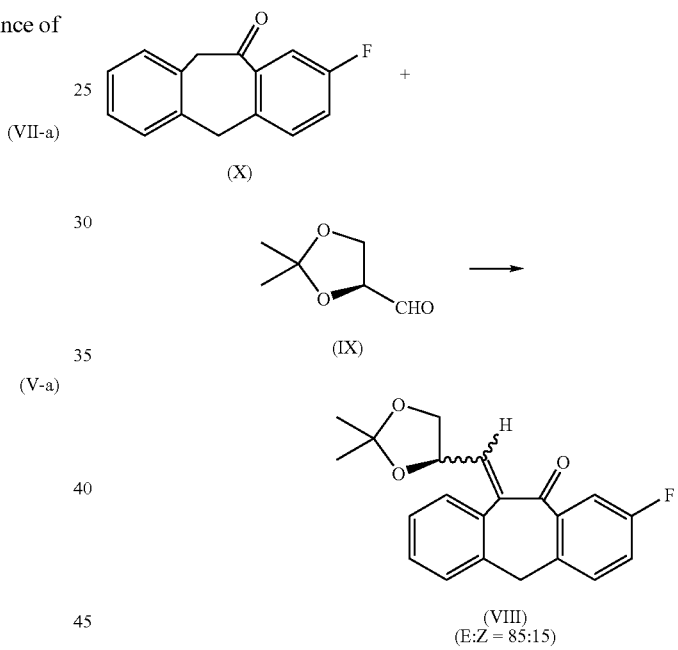

(VIII)
(E:Z = 85:15)

yielding unsaturated ketone (VIII) and reducing said unsaturated ketone to a mixture of epimeric ketones (VII-a) and (VII-b).

6. An intermediate compound of formula (I) having the formula

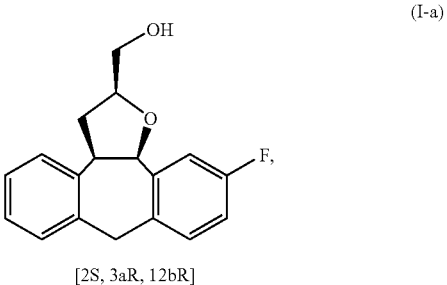

(I-a)

[2S, 3aR, 12bR]

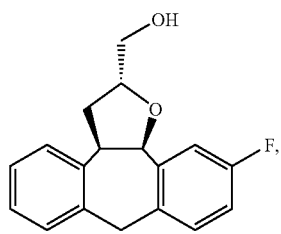

[2R, 3aR, 12bR]

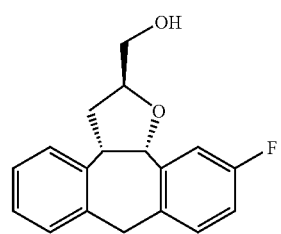

[2S, 3aS, 12bS]

or

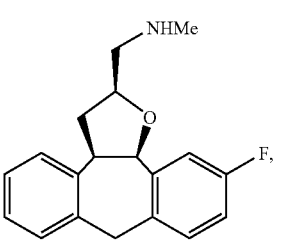

[2R, 3aS, 12bS]

7. A compound of formula (III) having the formula

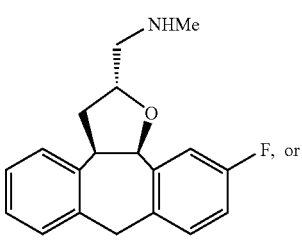

[2S, 3aR, 12bR]

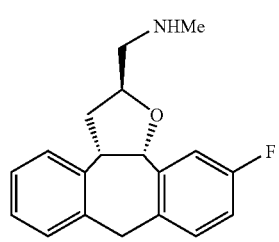

[2R, 3aR, 12bR]

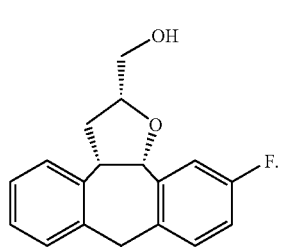

[2S, 3aS, 12bS]

in free base form or a pharmaceutically acceptable acid addition salt form thereof.

8. A compound of formula (III) according to claim 7 for use as a medicine.

9. A compound according to claim 8 for use as a CNS active medicine.

10. A pharmaceutical composition comprising a pharmaceutically effective amount of a compound of formula (III) as defined in claim 7 and a pharmaceutically acceptable carrier.

* * * * *